United States Patent [19]

Genese

[11] 4,320,889
[45] Mar. 23, 1982

[54] FLOW CONTROL DEVICE WITH ROLLER ORIENTATION MEANS

[75] Inventor: Joseph N. Genese, Waukegan, Ill.

[73] Assignee: Abbott Laboratories, North Chicago, Ill.

[21] Appl. No.: 150,503

[22] Filed: May 16, 1980

[51] Int. Cl.³ .............................................. F16K 7/06
[52] U.S. Cl. ...................................................... 251/6
[58] Field of Search ........................................ 251/6, 9

[56] References Cited

U.S. PATENT DOCUMENTS

| | | | |
|---|---|---|---|
| 3,630,481 | 12/1971 | McGay | 251/6 |
| 3,893,468 | 7/1975 | McPhee | 251/6 |
| 4,034,773 | 7/1977 | Huggins | 251/9 |
| 4,047,694 | 9/1977 | Adelberg | 251/6 |
| 4,177,969 | 12/1979 | Sieber-Müller | 251/9 |
| 4,238,108 | 12/1980 | Muetterties | 251/6 |

FOREIGN PATENT DOCUMENTS

| | | | |
|---|---|---|---|
| 188380 | 12/1936 | Switzerland | 251/9 |
| 1440995 | 6/1976 | United Kingdom | 251/6 |

*Primary Examiner*—H. Jay Spiegel
*Attorney, Agent, or Firm*—Robert L. Niblack; Neil E. Hamilton

[57] ABSTRACT

A flow control device for regulating the flow of fluid through a flexible tubing wherein a roller is employed with a grooved surface for incrementally controlling the flow of fluid through the tubing. In order to properly orientate the groove of the roller during its path of travel through the clamp body and over the tubing, a flat segment or interrupted surface portion is provided on the roller and an interfering member is provided in the base of the clamp. In addition, and to improve the efficiency of the clamp, additional features such as a relief surface in the roller, centering lugs for the tubing to position it in the clamp body, as well as circumferential ribs on the roller are provided.

8 Claims, 14 Drawing Figures

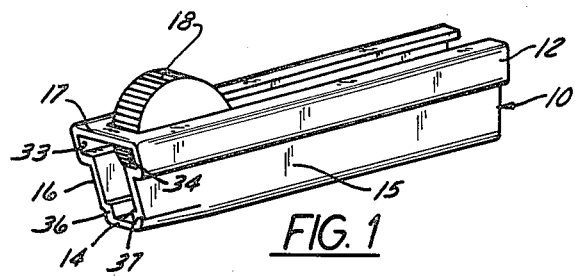
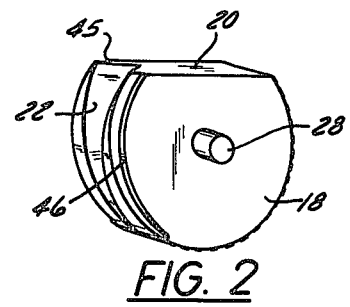
FIG. 1
FIG. 2
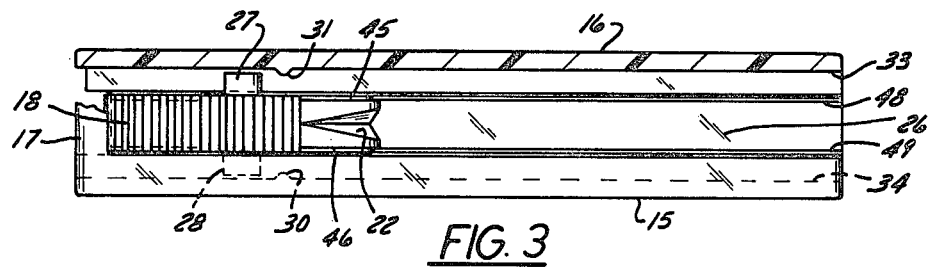
FIG. 3
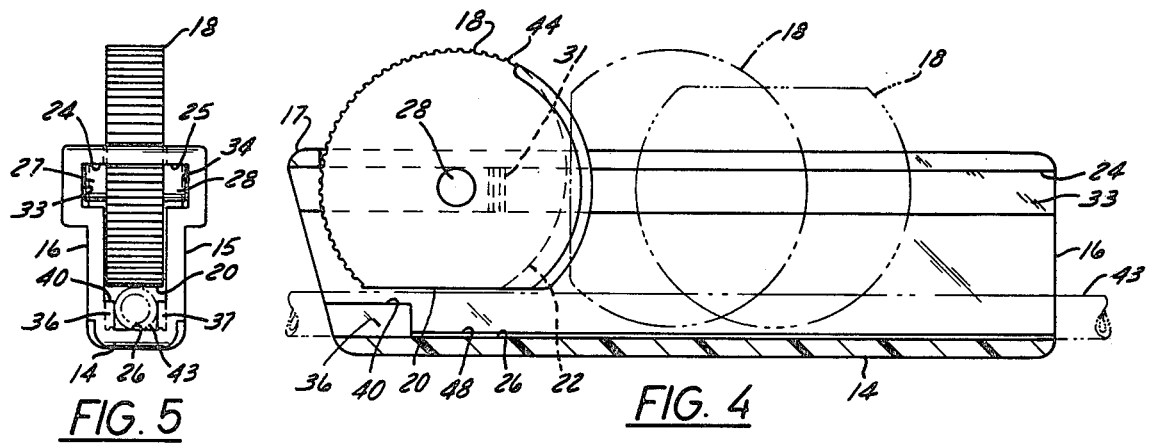
FIG. 5
FIG. 4
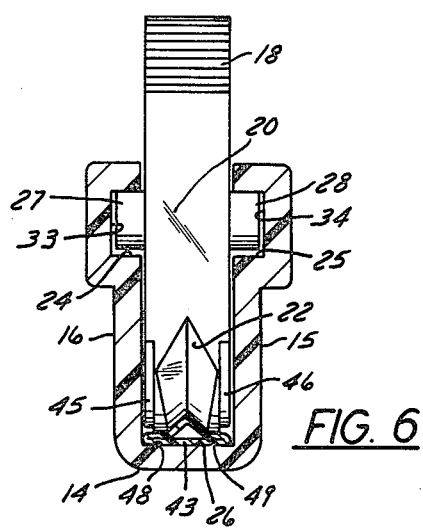
FIG. 6
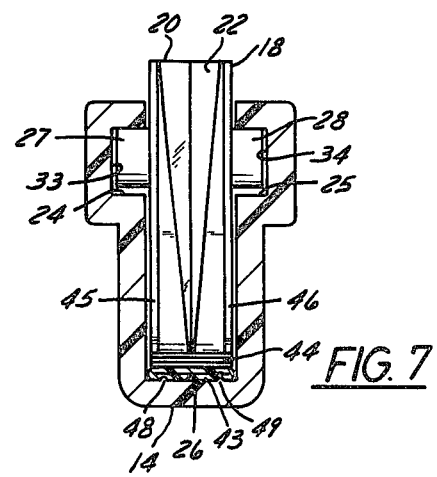
FIG. 7

FLOW CONTROL DEVICE WITH ROLLER ORIENTATION MEANS

BACKGROUND OF THE INVENTION

This invention relates to a flow control unit of the roller clamp type for accurately controlling the flow of fluid through a length of flexible tubing. More particularly, this invention relates to a combined clamp and flow control member wherein a groove is provided in the roller and which compresses the tubing against the floor of the clamp in an incremental manner through the variable dimension of the groove. The roller has a flat or interrupted portion which acts in conjunction with the surface in the floor to orientate the groove in the roller for movement over the tubing.

Clamping devices or flow control units of the type concerned with in this invention are disclosed in U.S. Pat. Nos. 3,893,468 and 4,047,694. In U.S. Pat. No. 3,893,468 a roller clamp is described which has a grooved surface for incrementally clamping a length of flexible tubing to control the flow rate as well as to stop the flow therein. However, no means are provided in this particular patent so that the groove in the roller can be properly orientated in conjunction with the tubing for its path of travel through the clamp body. In U.S. Pat. No. 4,034,773 a grooved surface is disclosed in a cam member for incrementally clamping flexible tubing. U.S. Pat. No. 4,047,694 does not describe a roller with any groove therein. However, it is referred to for showing laterally recessed areas in the roller surface to accommodate the tubing as it is compressed. The prior art nowhere teaches a flow control device wherein a grooved roller is properly orientated with respect to the tubing so that it will properly perform its function in incrementally pressing the tubing as it travels from one end of the clamp body to the other. Neither is there available a roller clamp with a varying groove in the surface of the roller which will accurately and incrementally compress the tubing within the precise specifications required for use in conjunction with an I.V. administration set.

It is an advantage of the present invention to provide a combined clamp and flow control member which can precisely control the flow of fluids through flexible I.V. tubing and can do so by means of a groove of progressively varying depth and width which is provided in the roller body. Other advantages are a flow control unit which is disposable, has means for orientating the groove in the roller with the clamp body, will position the tubing in the clamp body for controlled compression thereof, can be repositioned anywhere along the tubing, and can be fabricated without expensive molding procedures.

SUMMARY OF THE INVENTION

The foregoing advantages are accomplished and the shortcomings of the prior art are overcome by the present combined clamp and flow control member which includes a clamp body with a longitudinal axis and defining a surface for supporting a length of flexible tubing. Opposing walls extend from the surface and present a passage for the tubing. Guide surfaces are arranged in the walls for a rotatable member which is positioned to be guided and rotated along guide surfaces. A groove of progressivly varying depth and width extends peripherally around a portion of the rotatable member. Orientation means are operatively associated with the rotatable member in the clamp body to position the rotatable member in the clamp body and between the opposing walls so that the groove will be in immediate contact with the tubing support surface upon rotation of the rotatable member. In a preferred manner, the groove in the roller is positioned so that its largest dimension is in immediate contact with the tubing. Further, for improved flow control, portions of the roller are relieved laterally to permit the tubing to extend upwardly and lug members are disposed in the floor of the clamp or ribs on the roller surface to centrally position the tubing for controlled compression within the groove.

BRIEF DESCRIPTION OF THE DRAWINGS

A better understanding of the present clamp and flow control unit will be accomplished by reference to the drawings wherein:

FIG. 1 is a perspective view illustrating the flow control clamp member of this invention.

FIG. 2 is a perspective view of the roller for use in the clamp of FIG. 1.

FIG. 3 is a top plan view of the roller clamp of FIG. 1 with a portion broken away to illustrate the roller retention means as well as its path of travel over the guide surfaces.

FIG. 4 is a view in vertical section illustrating the orientation means for the roller prior to its travel over the tubing in the clamp body as well as illustrating the positioning of the roller during later travel.

FIG. 5 is an end view of the roller clamp of FIGS. 1 and 4 showing the orientation means in the clamp floor.

FIG. 6 is an end view in section of the roller clamp shown in FIG. 4 with the roller shown in the intermediate position illustrating the roller and the groove engaging the tubing.

FIG. 7 is a view similar to FIG. 5 except showing the roller clamp completely compressing the tubing and with the roller in an extreme right hand position.

DESCRIPTION OF THE PREFERRED EMBODIMENT

Figure 8:
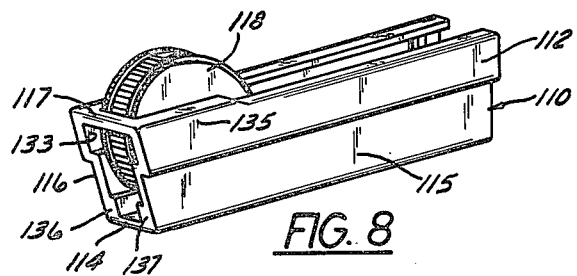
FIGS. 8–14 illustrate an alternative embodiment of the clamp of the present invention with FIGS. 8–14 corresponding to FIGS. 1–7, respectively.
Figure 9:
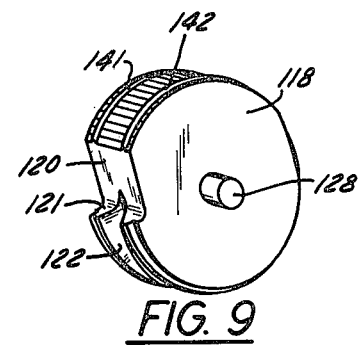
Figure 10:
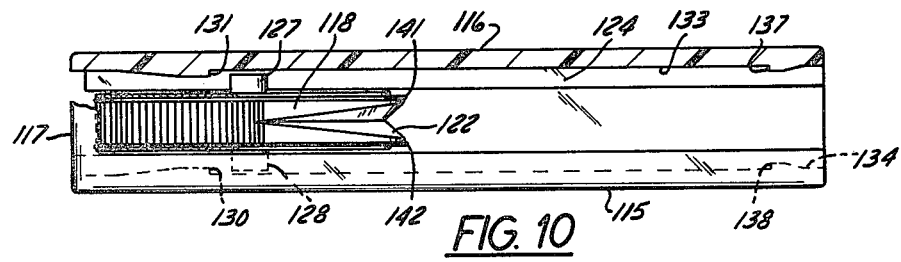

Proceeding to a detailed description of the preferred embodiment of the present invention, the flow control or clamp device, generally 10, includes a U-shaped body section 12 having a longitudinal axis with a base portion 14 and upwardly extending, opposing side walls 15 and 16. A bridge portion 17 extends between the side walls at the top of the clamp for stability purposes. A roller 18 is rotatably mounted in body section 12 and includes a flat segment 20 as well as a slot or groove of varying dimension 22, which slot terminates at one side of the flat section 20. Flat segment 20 extends completely across the roller in the form of a geometric chord. As best illustrated in FIG. 3, roller 18 includes trunions 27 and 28 for guidance in guide slots 33 and 34, respectively. Flanges 30 and 31 extend from side walls 15 and 16 adjacent the guide slots 33 and 34 for purposes of frictionally holding the roller within the clamp body once the trunions are passed between the flanges.

As best seen in FIGS. 4 and 5, block members 36 and 37 are positioned adjacent sidewalls 16 and 15 and extend upwardly from base portion 14 to present an interfering member or upper surface such as 40. Roller 18 is so dimensioned that when trunions 27 and 28 are placed in guide slots 33 and 34 that the flat or interrupted surface 20 of roller 18 will pass over the upper surfaces such as 40 of block members 36 and 37 but other portions of the roller will not. This serves as means to automatically orientate slot 22 in conjunction with I.V. tubing 43. Guide surfaces 24 and 25 will be contacted by trunions 27 and 28 for guidance of roller 18 over tubing 43.

As illustrated in FIGS. 6 and 7, roller 18 includes two relief portions 45 and 46 which extend laterally and adjacent slot 22. In addition, opposite block members 36 and 37 and positioned in base portion 14 are lugs 48 and 49 which extend upwardly from base 14 for purposes of centering the tubing for incremental compression in slot 22. It will be noted in FIGS. 6 and 7 that groove 20 has a configuration which varies in depth and width which incrementally decreases from flat portion 20 to the surface as indicated at 44.

ALTERNATIVE EMBODIMENT

FIGS. 8-14 illustrate an alternative embodiment of the flow control device with similar numbers in the "100" series being used to illustrate similar parts as in device 10.

The main difference between flow control device 10 and 110 is in the design of the flat segment 120 in that it does not extend completely across the roller as does flat segment 20 in roller 18, but extends only a partial distance terminating in slot 122 in a transverse manner to result in a transverse portion 121. Other differences are in the utilization of roller slots 133 and 134 having a slight upwardly extending projections such as illustrated at 135 in FIGS. 8 and 11 as well as circumferential ribs 141 and 142 in place of centering lugs for the tubing which are postioned in the floor in unit 10. In all other respects, the component parts of unit 110 are the same as unit 10 with the important element being the orientation means as provided by flat segment 120 and the upper surfaces 140 of block members 136 and 137.

OPERATION

A better understanding of the advantages of the flow control devices 10 and 110 will be had by a description of their operation. Referring to control device 10 first, roller 18 will be placed in U-shaped body 12 by placing trunions 27 and 28 in guide slots 33 and 34 at a position opposite ridge 17. This will be accomplished by pressing the trunions 27 and 28 past flanges 31 and 30 and rotating the roller until the flat segment 20 is positioned over upper surfaces 40. Prior to this positioning, tubing 43 will have been placed over the base portion 14 between block members 36 and 37 (as shown in FIG. 5) as well as between lugs 48 and 49 at the opposite end of the clamp body. The clamp will then assume a position as shown in FIG. 4. It will be noted that with the largest dimension of slot 22 placed closer to the flat surface 20 than the normal rounded surface shown at 44, the largest dimension will contact the tubing 43 after a slight rotation of the roller away from block members 36 and 37. To control the flow of fluid through the tubing such as when the tubing will be connected to the usual I.V. administration set, the roller will be initially rotated so that roller 18 will grip tubing 43 to cause trunions 27 and 28 to snap past flanges 30 and 31. Rotation of roller 18 will be continued to move the roller through the body section with groove 22 in contact with the tubing and will assume a position such as shown in FIG. 6. As the roller is moved continuously away from block members 36 and 37, the groove dimension of the roller will become less and less and accordingly, the flow through the tubing will become less and less until only the flat circumferential surface 44 of the roller will come in contact with the tubing to completely compress it and close off any flow therethrough. This is best seen in FIG. 7. It will be appreciated that as the roller moves over the tubing and portions of the tubing are moved laterally from the base clamping surface 26, relief areas 45 and 46 will accommodate any excess tubing. It will be further appreciated that the tubing will be accurately retained for incremental compression with groove 22 by means of the lateral surfaces of block members 36 and 37 and lugs 48 and 49.

Figures 11, 12:
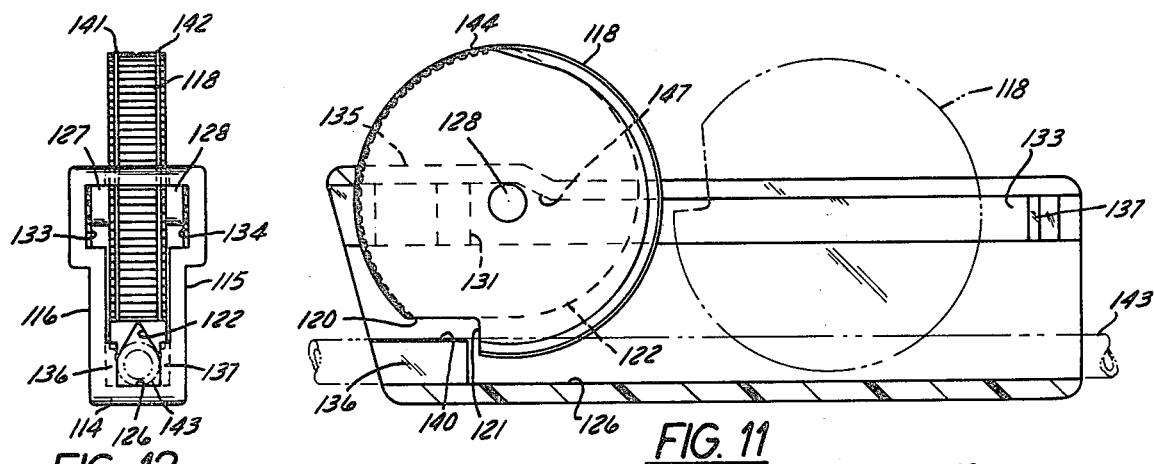
Figure 13:
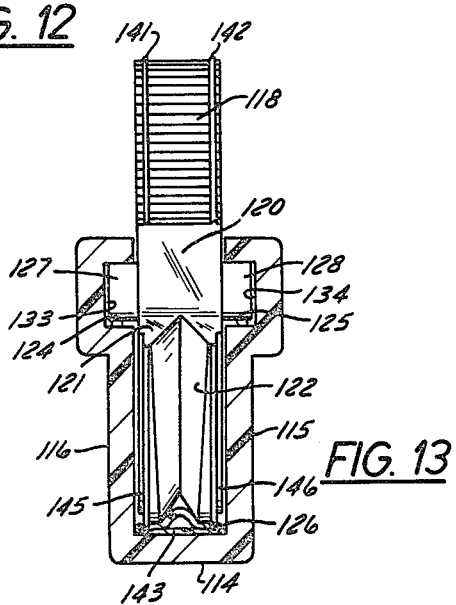
Figure 14:
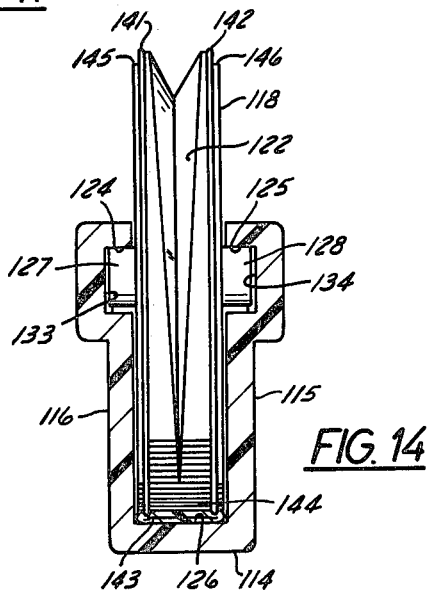

The operation of flow control unit 110 is bassically similar to that for unit 10 except that in providing a transverse portion 121 in the slot 122 immediately adjacent the flat segment 120, this provides for an automatic interferring type stop when the roller is placed over upper surfaces 140 of block members 136 and 137 for orientation purposes as best seen in FIG. 11. Also, in conjunction with unit 110, it will be appreciated that extensions such as 135 are provided for roller tracks 133 and 134 so that trunions 127 and 128 can ride upwardly therein for ease of placement of flat segment 120 of roller 18 thereover during the orientation. Subsequently, trunions 127 and 128 will ride downwardly over ramps such as 147 to position the roller at a lower level after it passes over block members 136 and 137. Another difference in the operation is in the utilization of the circumferential ribs 141 and 142 on roller 118 which will centrally position the tubing in the groove during compressive contact with the roller during its path of travel through the clamp body.

An important aspect of this invention is in the orientation means provided by the upper surfaces 40 or 140 of block members 36 and 37 or 136 and 137 of units 10 and 110, respectively. This orientation assures that grooves or slots 22 or 122 will immediately contact the tubing and the entire length of the control slots 22 or 122 will contact the tubing as the rollers 18 or 118 pass thereover in the clamp body. If it were not for this orientation means, it could never be determined as to when the slots 22 and 122 would contact the tubing which possibly could not take place throughout the length of the slot if, for example, a normal portion of the roller were to contact the tubing first and that portion would be adjacent the narrowest portion of the slot. Slots 22 and 122 have been shown as being of a generally V-shaped configuration with the depth of the slot and the angle thereof varying gradually over the circumference of the roller. As will be seen in conjunction with FIG. 7, slot 22 can be of a somewhat elongated diamond shape in that it will have increasing angle and an increasing depth to a point where it will reach a maximum angle and depth and then will assume a gradually lesser depth and angle until it diminishes to the normal surface of the roller. These particular angular and depth relationships for the slots are not critical and can be varied in any manner so as to effect controlled compression of the tubing in a manner such that there is lesser compression at the beginning of the travel of the roller when it is first orientated and then with incremental increasing compression as it moves away from the orientating block members. Ribs 141 and 142 are indicated as extending completely and circumferentially around roller 118. This is not essential as efficient, controlled compression of tubing 143 can be effected if ribs 141 and 142 extend only the length of slot 122.

As described earlier, walls 15 and 16 as well as 115 and 116 will flex outwardly to a slight degree when the trunions of the rollers are forced past flanges such as 30, 31, 130, 131 or 137 and 138 for loading purposes of the trunions in the roller slots. This is accomplished by reason of the fact that the materials for fabricating the walls is a semirigid plastic material, preferably acrylonitrile-butadiene-styrene. If desired, other polymeric materials such as polycarbonate or polyvinyl chloride can be utilized. The flow control units 10 and 110 are completely disposable and consequently the rollers 18 and 118 could be formed from the same material as the clamp bodies 12 and 112.

It will thus be seen that through the present invention there is now provided a flow control unit having a flow control groove or slot in the rotatable member which can be precisely orientated in the clamp body. The rotatable member is automatically orientated in the clamp body by means of a specific geometric configuration provided in the roller as well as ledge or surface means disposed in the floor of the clamp. The orientation means is provided without appreciable cost in the fabrication, yet it will permit ease of assembly, both without expensive molds or excessive assemblying procedures. The flow control units are completely disposable, yet are readily adapted to being operated by a single hand movement.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

We claim:

1. A flow control device for regulating flow through a length of flexible tubing comprising:
    a clamp body having a longitudinal axis and defining a surface for supporting a length of flexible tubing;
    opposing walls extending from said surface and presenting a passage for said tubing;
    guide surfaces arranged in said walls;
    a rotatable member guided, rotated and moveable longitudinally along said guide surfaces;
    a groove of progressively varying depth extending peripherally around a portion of said rotatable member;
    orientation means defined as a portion of said rotatable member and said clamp body to position said rotatable member in said clamp body and between said opposing walls so that said groove will be held in immediate contact with said tubing to press said tubing against said support surface upon rotation of said rotatable member wherein said rotatable member is defined by a roller member and said orientation means is defined by an interfering member extending from said supporting surface and a complementary section formed as a portion of said rotatable member so that said complementary section of said roller member will pass over said interfering member and will permit rotation of said roller member after passage thereover; and wherein said interfering member is defined by at least one block member adjacent one of said opposing walls and said complementary section is defined by a flat segment provided in said roller member adjacent said groove.

2. The tubing clamp as defined in claim 1 wherein said flat segment is positioned closer to the widest dimension of said groove.

3. The tubing clamp as defined in claim 2 wherein said flat segment extends completely across said roller member and in the form of a geometric chord.

4. The tubing clamp as defined in claim 2 wherein said flat segment joins said groove by means of a second flat segment and transversely thereto.

5. The tubing clamp as defined in claim 1 wherein said rotatable member further includes opposed relieved sections positioned adjacent said groove and circumferentially of said roller.

6. The tubing clamp as defined in claim 1 further including rib members extending circumferentially from said roller member and adjacent said groove.

7. The tubing clamp as defined in claim 1 wherein said rotatable member includes trunions for rotation in said guide surfaces and further including frictional engagement means operatively associated with said guide surfaces for contact with said trunnions for retention thereof in said guide surfaces.

8. The tubing clamp as defined in claim 1 wherein said guide surfaces are defined by a guide track, said guide track including a ramp surface operatively positioned with respect to said orientation means to position said rotatable member in said clamp body at a lower level after said rotatable member passes over said interfering member in said clamp body.

* * * * *